United States Patent [19]

Witiak et al.

[11] Patent Number: 4,950,755
[45] Date of Patent: Aug. 21, 1990

[54] BIS(MORPHOLINOMETHYL) DERIVATIVE OF 1,2-BIS(DIOXOPIPERIZINYL)PROPANE

[75] Inventors: Donald T. Witiak, Mt. Vernon; Hattiangadi B. Bhat, Columbus, both of Ohio

[73] Assignee: Ohio State University, Columbus, Ohio

[21] Appl. No.: 251,102

[22] Filed: Sep. 28, 1988

Related U.S. Application Data

[63] Continuation of Ser. No. 764,484, Aug. 12, 1985, abandoned.

[51] Int. Cl.$^5$ ............................................. C07D 413/12
[52] U.S. Cl. ..................................................... 544/82
[58] Field of Search ........................................ 544/82

[56] References Cited

FOREIGN PATENT DOCUMENTS 125475  11/1984  European Pat. Off. ............. 544/82

OTHER PUBLICATIONS

Ren et al., *Kexue Tongbao*, 1980:25, 189.
Chemical Abstracts vol. 102 (1985) No. 149288g (Abstract of JP59, 190 976, 29 Oct. 1984).

*Primary Examiner*—Robert W. Ramsuer
*Attorney, Agent, or Firm*—Emch, Schaffer, Schaub & Porcello Co.

[57] ABSTRACT

Bis(morpholinomethyl) derivative of 1,2-bis(dioxopiperizinyl)propane of the formula:

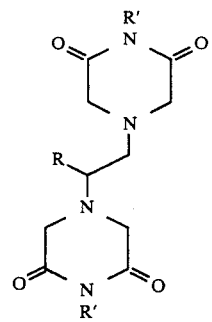

wherein R is $CH_3$, R' is

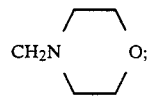

and the process for the synthesis thereof is provided. The compound of the present invention is water soluble, may be administered by intravenous injection and lessens the severity of doxorubicin-induced cardiotoxicity.

1 Claim, No Drawings

BIS(MORPHOLINOMETHYL) DERIVATIVE OF 1,2-BIS(DIOXOPIPERIZINYL)PROPANE

This is a continuation of co-pending application Ser. No. 764,484 filed on Aug. 12, 1985, abandoned.

BACKGROUND OF THE INVENTION

Bis(dioxopiperazines) are considerable import owing to their antimetastatic properties and their actions ameliorating anthracycline-induced toxicity in animals as reported by Herman et al., 19 *Adv. in Pharmacol. and Chemother.*, 249 (1982).

A morpholinomethyl analogue of the bis(dioxopiperazine) compound known as 1CRF#154 and herein after referred to as Compound I, namely bis-4-morpholinomethyl-3,5-dioxopiperazinyl-1,2-ethane) also known as "bimolane" and hereinafter referred to as Compound II was reported by Ren et al., *Kexue Tongbao*, 1980:25, 189, to be active, by both the oral and ip routes, against various experimental tumors. Results of the clinical investigations in China indicated that this bimolane, Compound II, may be useful in the treatment of malignant lymphomas, uveitis, sympathetic ophthalmitis and psoriasis (Ren et al., supra). The correlation between the structure of morpholinomethyl-N groups and their behavior in vivo is not well-understood and there is a continuing need for the development of pharmacologically and clinically effective bis(morpholinomethyl) derivatives of bis(dioxopiperazines).

Bimolane (Compound II) is insoluble in water and therefore cannot be employed by intravenous injection. Additionally, it is unclear what is responsible for its antitumor activity since crystals of this material contain Compound I which is the unsubstituted bis(dioxopiperazine( [Camerman et al., *Science* 225, 1165 (1984)].

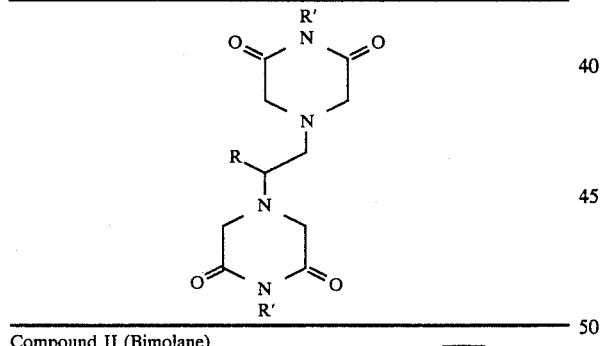

Compound II (Bimolane)

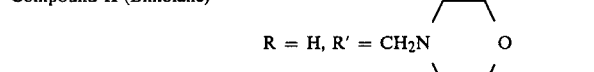

Compound V

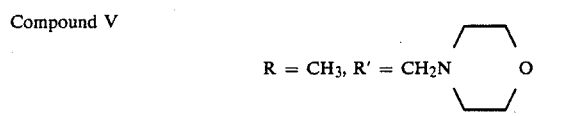

| Compound I (ICRF #154) | R = H, R' = H |
| Compound III (ICRF #159) | R = CH₃, R' = H (dl) |
| Compound IV (ICRF #187) | R = CH₃, R' = H (d) |

A major limitation to the effective clinical use of daunorubicin or doxorubicin is dose-related cardiomyopathy. Lefrak, E. A.; Pitha, J.; Rosenheim, S.; Gottlieb, J. A., *Cancer*, (Phil.) 34, 302-314 (1973)][Lefrak, E. A.; Pitha, J.; Rosenheim, S.; O'Brian, R. M.; Burgess, M. A.; Gottlieb, J. A. *Cancer Chemother. Repts.*, 6, 203-208 (1975)]. There is evidence to indicate that bis(-dioxopiperazines) can modify daunorubicin or doxorubicin toxicity. In previous studies, pretreatment with 1,2-bis(dioxopiperazinyl)propane (dl) (1CRF#159) (Compound III) caused a significant reduction in high-dose daunorubicin toxicity. [Herman, E. H.; Mhatre, R. M.; Chadwick, D. P. *Tox. Appl. Pharmacol.*, 27, 517 (1974)]. Compound IV (ICRF#187), the more water soluble d isomer of Compound III also reduces the acute toxicity of high doses of daunorubicin. [Herman, E. H.; Ardalan, B.; Bier, C.; Waravdekar, V.; Krop, S. *Cancer Treat. Repts.*, 63, 89 (1979)]. Pretreatment with Compound IV was found to reduce cardiac toxicity in rabbits [Herman, E. H.; Ferrans, V. J.; Jordan, W.; Ardalan, B. *Res. Comm. Chem. Path. Pharmacol.*, 31, 85 (1981)], miniature pigs [Herman, E. H.; Ferrans, V. J. *Lab. Invest.*, 49, 69-77 (1983)], and beagle dogs [Herman, E. H.; Ferrans, V. J. *Cancer Res.*, 41, 3436-3440 (1981)] treated chronically with daunorubicin or doxorubicin. Thus, there is a need for a water soluble bis(dioxopiperazine) which is pure and remains active as an agent which ameliorates anthracycline-induced cardiotoxicity in mammals.

SUMMARY OF THE INVENTION

The invention relates to the novel bis(morpholinomethyl) derivative of the compound 1,2-bis(dioxopiperizinyl)propane, which is a compound of the formula:

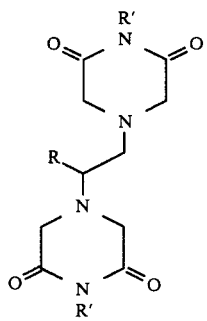

wherein

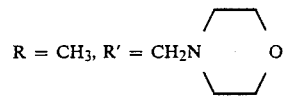

(Compound V). The compound of the present invention can be prepared as a pure water soluble solid.

The present invention further relates to a process for the synthesis of the bis(morpholinomethyl) derivative of the compound 1,2-bis(dioxopiperizinyl) propane.

This invention further relates to a method for protecting mammals from doxorubicin-induced cardiotoxicity, comprising administering to a mammal being treated an amount of the foregoing compound, in admixture with a physiologically and pharmaceutically acceptable carrier, which inhibits cardiotoxicity in mammals being treated with doxorubicin. The foregoing compound is effective in protecting mammals from doxorubicin-induced cardiotoxicity when the foregoing compound is administered prior to doxorubicin.

DESCRIPTION OF THE INVENTION

The compound provided in accordance with the invention is the bis(morpholinomethyl) derivative of the compound 1,2-bis(dioxopiperazinyl)propane, which has the formula:

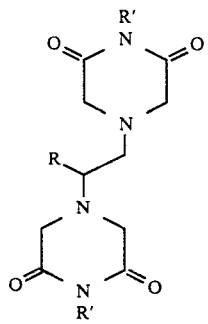

wherein R is $CH_3$, R' is

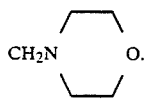

The compound is synthesized by admixing a compound of the general formula above wherein R is $CH_3$, R' is H with DSMO (dimethylsulfoxide) to form a mixture. The mixture is stirred at approximately 55° 1 C. and a filtrate is then recovered. Morpholine and formaldehyde solution are admixed with the filtrate to form a second mixture. The second mixture is stirred at approximately 50° C. for 1 hour and for 20 hours at 26° C. and a crystalline solid, the compound of the present invention, is recovered.

Suprisingly, administration of a combination of the compound of the present invention and doxorubicin to mammals, greatly lessened the number and severity of cardiac lesions in the treated mammals.

Further, there were no morphologic alteration in the mammals' kidney, lung, small intestine or diaphram that are attributable to doxorubicin or the compound of the present invention.

BIOLOGICAL EVALUATION

Beagle dogs (1 to 1.5 years old) of either sex, weighting between 6.2 to 11.4 kg were divided into 2 groups of 8 animals, 1 group of 5 animals (3rd group) and 1 group of 3 animals (4th group). The dogs in groups 1 and 2 received intravenous injections of 1.75 mg/kg doxorubicin once every 3 weeks. The animals in group 2 were pretreated 30 minutes before doxorubicin administration with an intravenous injection of 25.0 mg/kf of Compound V. The animals in group 3 were given 25.0 mg/kg Compound V and the animals in group 4 were given saline without doxorubicin. Compound V and doxorubicin were dissolved in physiologic saline just before use and injected as a 20 mg/ml and 10 mg/ml solution, respectively. A total of 8 intravenous injections of doxorubicin were given to non-pretreated animals and 9 doxorubicin injections were given to Compound V pretreated animals.

After each injection, the animals were returned to their cages, observed daily and weighed weekly. Three weeks after the 8th or 9th injection (total doxorubicin dose 14.0 to 15.75 mg/kg) the dogs were killed with overdose of pentobarbital sodium; the entire heart and samples of liver, kidney, small intestine, diaphram and lung were excised and fixed in 10% neutral formalin. Blocks of heart tissue were embedded in glycomethacrylate plastic resin. Sections of the left ventricular free wall and left ventricular anterior and posterior papillary muscles were prepared and stained with hematoxylin-eosin and toluidine blue. All other tissues were embedded in paraffin and stained with hematoxylin-eosin.

The frequency and severity of doxorubicin-induced cardiac lesions were assessed by light microscopic examination of the 3 left ventricular sections. The changes were graded on a scale of 0 to 4+ on the basis the numbers of muscle cells showing myofibrillar loss and cytoplasmic vacuolization in which 0=no damage; 1+=involvement of only an occasional cell; 4+= involvement of 50% or more cells in the visual field; and 2+ and 3+=intermediate degrees of involvement. A single score was given after evaluating all 3 tissue sections. Differences in the severity scores between the groups were analyzed by the chi-square test. The results of the biological evaluation are as follows:

CLINICAL SIGNS AND WEIGHT CHANGES

A total of 5 dogs given doxorubicin alone died before the end of the study. Two of these animals had received 7 injections and 3 others dies 1 to 2 weeks after the 8th dosing. The remaining 3 were euthanized 3 weeks after the 8th dose. None of the animals given the combination of Compound V and doxorubicin died before the end of the study (3 weeks after the 9th dosing).

Except for alopecia, the 1.75 mg/kg dose of doxorubicin had little overt effects on the dogs. By the 4th dose, alopecia was noted around the limbs. As dosing continued, the alopecia spread to the head, trunk and tail. Similar effects were noted in the dogs given the combination of Compound V and doxorubicin. Animals receiving Compound V alone did not show this effect.

A rapid bolus injection of Compound V caused some of the dogs to immediately lie down. This phenomena lasted less than 5 minutes after which the animals appeared entirely normal. These effects were not noted if the injection period was extended to 1 minute.

A temporary reduction in food consumption was noted during the first 24 hours after doxorubicin administration, regardless of pretreatment with Compound V. During the course of the studies the dogs receiving only Compound V increased in body weight from 9.4 to 11.0 kg; animals receiving doxorubicin alone lost an average of 0.8 kg (from 9.4 to 8.6 kg) and those receiving Compound V and doxorubicin gains an average of 1.6 kg (from 9.4 to 11.0 kg). Saline control dogs gained an average of 0.8 kg (from 10.3 to 11.1 kg).

MYOCARDIAL ALTERATIONS

The cardiac lesions observed in the present study were comparable to those observed previously in doxorubicin-treated humans, dogs, rabbits and pigs. The lesions showed two characteristics, cytoplasmic vacuolization and myofibrillar loss. Both of these changes involved progressively larger numbers of cells as lesions increased in severity. The vacuolization involved the formation of multiple clear membrane-limited vacuoles that filled the cytoplasm of the affected cells and caused them to appear larger than normal. The myofibrillar loss resulted in a pale but nonvacuolated appearance of the cytoplasm. Both types of change often coexisted in the same cells. Animals given doxorubicin alone showed the most severe cardiac alterations. All 8 animals from this group had a lesion core of 3+ (Table 1). In contrast, lesions were absent in the hearts of 3 to 8 dogs given the combination of Compound V and doxorubicin. A lesion score of 1+ were observed in 4 other animals. One Compound V pretreated dog had a 2+ lesion. The difference in severity of cardiomyopathy scores between the group given doxorubicin together with Compound V was highly significant (P<0.01) (Table 1). No cardiac lesions were present in animals receiving Compound V or saline alone.

PATHOLOGY OF NONCARDIAC TISSUES

At the dosage schedules used there were no morphologic alterations in kidney, lung, small intestine or diaphram that were attributable to doxorubicin or Compound V.

Pretreatment with Compound V caused a significant reduction in doxorubicin cardiotoxicity. One important effect was that the hearts of 3 of the 8 dogs pretreated with Compound V remained essentially normal despite the 9 injections of doxorubicin. This finding is all the more striking since a lower dose of doxorubicin caused severe lesions in all dogs which were not pretreated with Compound V. A second aspect of this protection was noted in the frequency and extent of the alterations in the remaining 5 animals. Vacuolization and myofibrillar loss in 4 of these animals occurred to only a minimal extent; even the changes found in the 5th animal with a lesion score of 2+ were less extensive than the lesions seen in any of the animals given doxorubicin alone.

A reduction in severity of cardiomyopathy could leas to an increase in the tolerated dose of doxorubicin. This possibility has not been examined in the present studies, but it should be noted that 5 to 8 animals given doxorubicin died after receiving 7 to 8 doses, whereas all the animals pretreated with Compound V survived 9 doxorubicin doses.

TABLE I

Effect of pretreatment with Compound V on the incidence and severity of doxorubicin-induced chronic cardiomyopathy in dogs.

| Treatment Group[a] | Incidence Dead/Lesions | Cardiomyopathy Score | | | | |
|---|---|---|---|---|---|---|
| | | 0 | 1 | 2 | 3 | ≦2[b] |
| Saline Control | 0/3 | 0/3 | 3 | 0 | 0 | 0 | 3/3 |
| Compound V Control | 0/5 | 0/5 | 3 | 0 | 0 | 0 | 5/5 |
| Doxorubicin | 5/8 | 8/8 | 0 | 0 | 0 | 8 | 0/8[c] |
| Compound V/ | 0/8 | 5/8 | 3 | 4 | 1 | 0 | 8/8 |

TABLE I-continued

Effect of pretreatment with Compound V on the incidence and severity of doxorubicin-induced chronic cardiomyopathy in dogs.

| Treatment Group[a] | Incidence Dead/Lesions | Cardiomyopathy Score | | | | |
|---|---|---|---|---|---|---|
| | | 0 | 1 | 2 | 3 | ≦2[b] |
| Doxorubicin[a] | | | | | | |

[a]Dogs were given 25.0 mg/kg Compound V intravenously or saline 30 minutes before 1.75 mg/kg doxorubicin intravenously every three weeks. Surviving dogs receiving doxorubicin alone were euthanitized three weeks after the 8th injection and those pretreated with Compound V three weeks after the 9th injection.
[b]Where ratios are given, the numerator denotes the number of animals with a cardiomyopathy score equal to or less than two and the denominator denotes the number of animals examined.
[c]Severity scores of doxorubicin group significantly greater than that of Compound V/Doxorubicin group by Chi square analysis (p < 0.01).

The following example is illustrative of the compounds within the scope of the invention:

1,2-bis(dioxopipperizinyl)propane (3.5 g., 13.0 mmol) was dissolved in dimethylsulfoxide (35 ml) by stirring at 55° C. and filtered. To the filtrate was added morpholine (3.5 g., 40 mmol) and 37% formaldehyde solution (3.5 ml, 40 mmol). The mixture was stirred at 55° C. for 1 hr and for 20 hours at 26° C. The crystalline solid that separated was stirred with ether (50 ml) containing ethanol (10 ml) and filtered. The solid was washed with ether affording 4.9 g. (81.7%) pure Compound V, m p 169°–170° C. Anal. calcd. for $C_{21}H_{34}N_6O_6$: C, 54.05; H, 7.36; N, 18.02. Found: C, 53.92; H, 7.20; N, 18.05. NMR ($CDCl_3$) 4.70 (4, s,2-$NCH_2N$), 4.05 (1,s, HC($CH_3$)$CH_2N$—), 3.50 (16, m, 2 morpholine $CH_2$, 2.90 (2, m, H($CH_3$)$CCH_2N$—), 2.50 (8, m, 2 diketopiperazine $CH_2$, 1.00 (3, d, $CH_3$, J=6.40 Hz).

As will be evident to those skilled in the art, various modifications of this invention can be made or followed in the light of the foregoing disclosure and discussion without departing from the spirit and scope of the disclosure or from the scope of the claims.

What we claim is:

1. A water soluble compound of the formula:

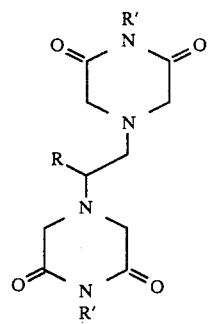

wherein R is $CH_3$,

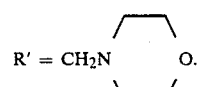

* * * * *